United States Patent
Li et al.

(10) Patent No.: US 12,419,728 B2
(45) Date of Patent: Sep. 23, 2025

(54) TOOTHBRUSH STERILIZING ASSEMBLY AND ELECTRIC TOOTHBRUSH

(71) Applicant: LUXSHARE PRECISION INDUSTRY CO., LTD., Shenzhen (CN)

(72) Inventors: Huabing Li, Shenzhen (CN); Zhongyuan Lai, Shenzhen (CN); Yu Huang, Shenzhen (CN); Zhexian Tianzhou, Shenzhen (CN)

(73) Assignee: LUXSHARE PRECISION INDUSTRY CO., LTD., Shenzhen (CN)

( * ) Notice: Subject to any disclaimer, the term of this patent is extended or adjusted under 35 U.S.C. 154(b) by 671 days.

(21) Appl. No.: 17/750,770

(22) Filed: May 23, 2022

(65) Prior Publication Data
US 2023/0127030 A1 Apr. 27, 2023

(30) Foreign Application Priority Data
Oct. 25, 2021 (CN) .......................... 202122570214.0

(51) Int. Cl.
| | |
|---|---|
| A61C 19/02 | (2006.01) |
| A61C 17/22 | (2006.01) |
| A61L 2/10 | (2006.01) |

(52) U.S. Cl.
CPC ............. *A61C 19/02* (2013.01); *A61C 17/22* (2013.01); *A61L 2/10* (2013.01)

(58) Field of Classification Search
CPC . A61C 19/02; A61C 17/22; A61L 2/10; A61L 2202/14
See application file for complete search history.

(56) References Cited

U.S. PATENT DOCUMENTS

| | | | | |
|---|---|---|---|---|
| 757,885 | A | * 4/1904 | Cochrane | ............... B44D 3/125 |
| | | | | 206/209 |
| 4,973,847 | A | * 11/1990 | Lackey | ..................... A61L 2/10 |
| | | | | 250/455.11 |

FOREIGN PATENT DOCUMENTS

| | | | |
|---|---|---|---|
| CN | 209712689 U | * | 12/2019 |
| CN | 211381922 U | * | 9/2020 |

(Continued)

OTHER PUBLICATIONS

CN 211381922 U English Translation (Year: 2019).*
(Continued)

*Primary Examiner* — Maris R Kessel
*Assistant Examiner* — Nebyate Seged
(74) *Attorney, Agent, or Firm* — Birch, Stewart, Kolasch & Birch, LLP

(57) ABSTRACT

Provided are a toothbrush sterilizing assembly and an electric toothbrush. The toothbrush sterilizing assembly includes a sterilizing shell, a sterilizing cover, a sterilizing element, a control module and a power supply module. The sterilizing shell has a cylindrical shape and is sleeved outside an electric toothbrush. The sterilizing cover is detachably connected to one end of the sterilizing shell and is capable of covering the one end of the sterilizing shell. The sterilizing element is disposed on an inner wall of the one end of the sterilizing shell. The control module is connected to the sterilizing element and configured to control the sterilizing element to start to sterilize a brush head of the electric toothbrush. The power supply module is electrically connected to the control module.

12 Claims, 7 Drawing Sheets

(56) References Cited

FOREIGN PATENT DOCUMENTS

CN         212345734 U   *   1/2021
CN         213371645 U   *   6/2021

OTHER PUBLICATIONS

CN 213371645 U English Translation (Year: 2020).*
CN 209712689 U English Translation (Year: 2018).*
CN212345734 U (English/Original Translation) (Year: 2021).*

* cited by examiner

TOOTHBRUSH STERILIZING ASSEMBLY AND ELECTRIC TOOTHBRUSH

CROSS-REFERENCE TO RELATED APPLICATION(S)

This application claims priority to Chinese Patent Application No. 202122570214.0 filed Oct. 25, 2021, the disclosure of which is incorporated herein by reference in its entirety.

TECHNICAL FIELD

The present disclosure relates to the field of cleaning products and, in particular, to a toothbrush sterilizing assembly and an electric toothbrush.

BACKGROUND

At present, the service life of the electric toothbrush's brush head is usually one month. In the existing art, in order to prevent sundries such as dusts, the bacteria or the like from falling on the brush head, a cover is usually mounted on the brush head, and the users can mount the cover on the brush head after brushing teeth. However, since the brush head is usually wet after being used, the brush head is still easy to breed bacteria, which affects the oral health of the users.

SUMMARY

The present disclosure aims to provide a toothbrush sterilizing assembly and an electric toothbrush, which can prevent sundries such as dusts from falling on the brush head, and prevent the bacteria from breeding on the brush head, thereby ensuring the oral health of users.

As conceived as above, the present disclosure provides the solution described below.

Provided is a toothbrush sterilizing assembly, including a sterilizing shell, a sterilizing cover, a sterilizing element, a control module and a power supply module.

The sterilizing shell has a cylindrical shape and is sleeved outside an electric toothbrush.

The sterilizing cover is detachably connected to one end of the sterilizing shell and is capable of covering the one end of the sterilizing shell.

The sterilizing element is disposed on an inner wall of the one end of the sterilizing shell.

The control module is connected to the sterilizing element and configured to control the sterilizing element to start to sterilize a brush head of the electric toothbrush.

The power supply module is electrically connected to the control module.

Further provided is an electric toothbrush, including a handle, a brush head and the toothbrush sterilizing assembly described above, where the sterilizing shell of the toothbrush sterilizing assembly is sleeved outside the brush head, and the sterilizing element is configured to sterilize the brush head.

REFERENCE LIST

Figure 1:
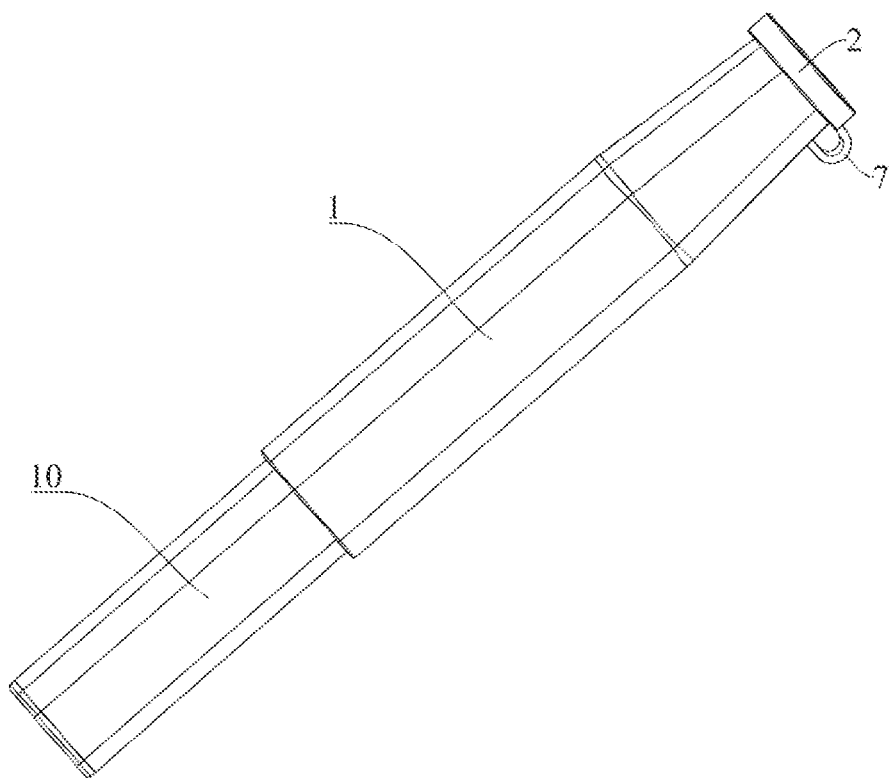
FIG. 1 is a schematic diagram of an electric toothbrush in a sterilizing mode according to an embodiment of the present disclosure.

1—sterilizing shell; 11—cylindrical body; 12—conical body;
2—sterilizing cover; 3—sterilizing element; 4—control module; 5—power supply module; 6—raised rib; 7—connecting part; and
10—handle; 20—brush head; and 30—photosensitive element.

DETAILED DESCRIPTION

To better illustrate the solved problem, adopted solutions and achieved effects of the present disclosure, the present disclosure is further described in conjunction with drawings and embodiments. It is to be understood that the embodiments set forth below are intended to merely illustrate and not to limit the present disclosure. For ease of description, only a part, not all, related to the present disclosure is illustrated in the drawings.

In the description of the present disclosure, it is to be noted that the orientations or position relations indicated by terms such as "center", "upper", "lower", "left", "right", "vertical", "horizontal", "inside", "outside" and the like are based on orientations or position relations shown in the drawings. These orientations or position relations are intended merely to facilitate and simplify the description of the present disclosure, and not to indicate or imply that a device or element referred to must have such specific orientations or must be configured or operated in such specific orientations. Thus, these orientations or position relations are not to be construed as limiting the present disclosure. In addition, terms such as "first" and "second" are used only for the purpose of description and are not to be construed as indicating or implying relative importance.

In the description of the present disclosure, it is to be noted that unless otherwise expressly specified and limited, the term "installation", "connected to each other", or "connected" is to be construed in a broad sense, for example, as securely connected or detachably connected; mechanically connected or electrically connected; directly connected to each other or indirectly connected to each other via an intermediary, or internally connected between two elements. For those of ordinary skill in the art, specific meanings of the preceding terms in the present disclosure may be understood based on specific situations.

This embodiment provides a toothbrush sterilizing assembly, which is used for sterilizing a brush head 20 of an electric toothbrush, and can prevent sundries such as dusts from falling on the brush head 20, and also prevent the bacteria from breeding on the brush head 20.

Figure 2:
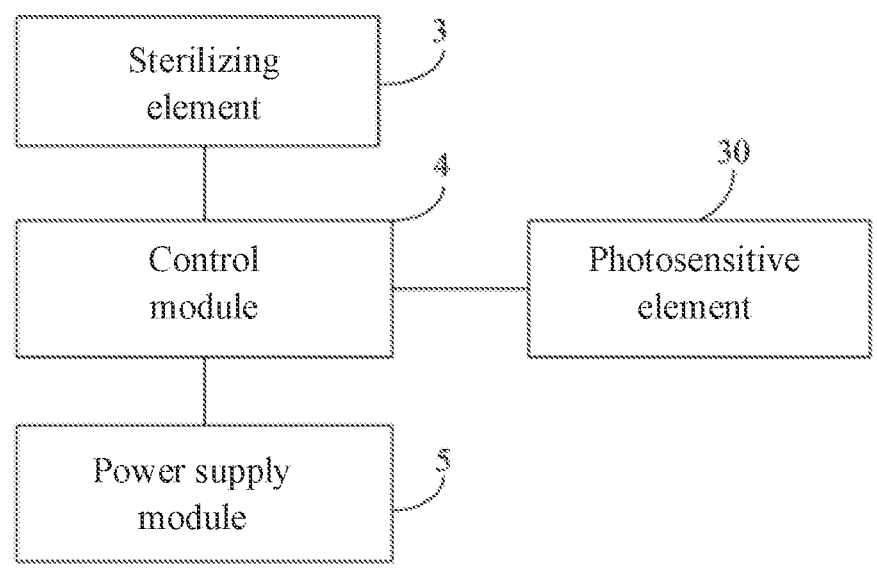
FIG. 2 is a schematic diagram of connections between a control module, a power supply module, a sterilizing element and a photosensitive element according to an embodiment of the present disclosure.

As shown in FIGS. 1 and 2, the toothbrush sterilizing assembly includes a sterilizing shell 1, a sterilizing cover 2, a sterilizing element 3, a control module 4 and a power supply module.

Figure 8:
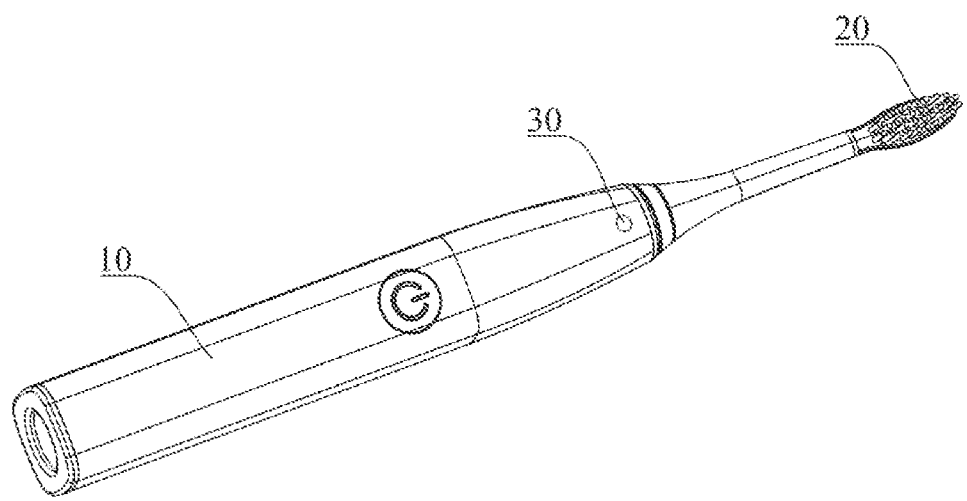
FIG. 8 is a structural diagram of a handle, a brush head and a photosensitive element according to an embodiment of the present disclosure.
Figure 9:
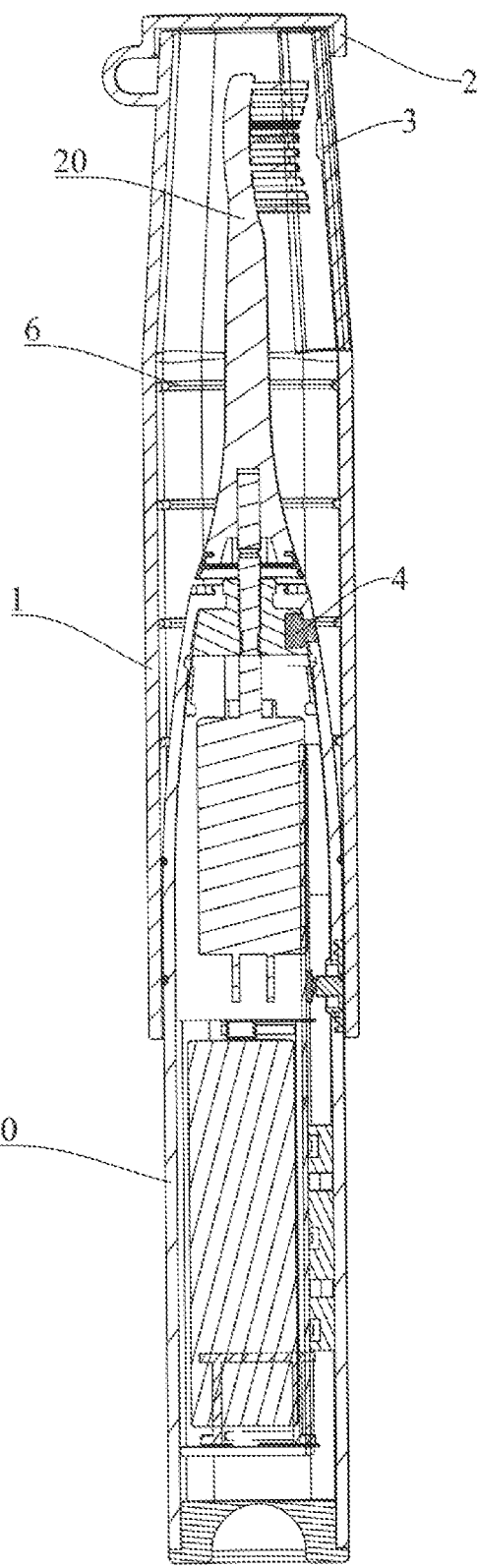
FIG. 9 is sectional view one of an electric toothbrush according to an embodiment of the present disclosure.
Figure 10:
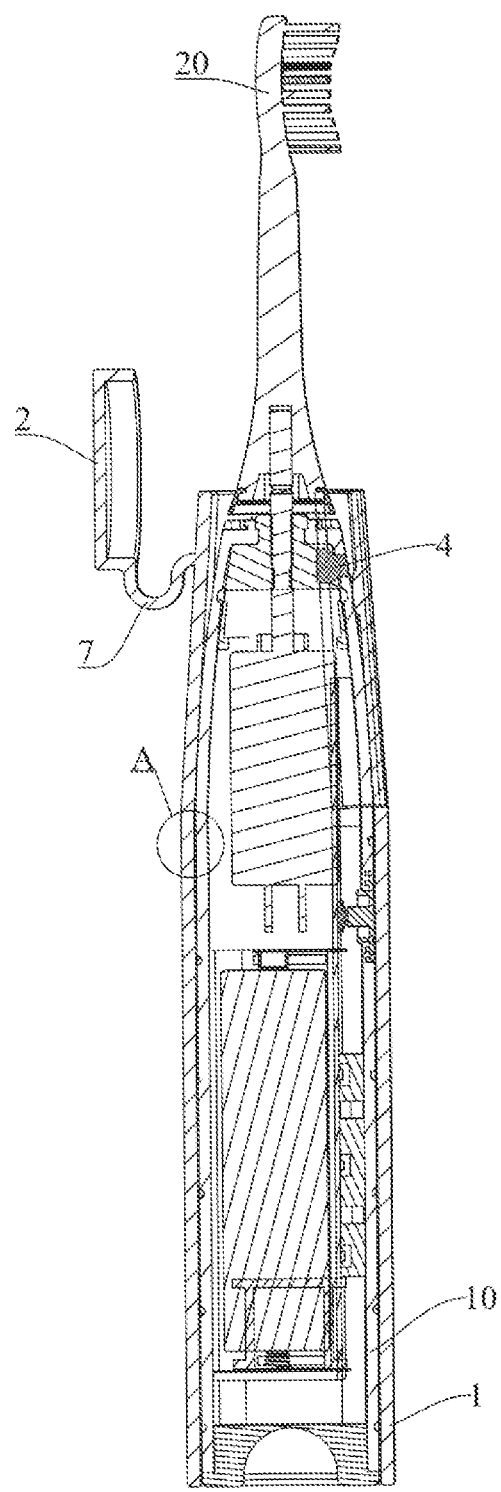
FIG. 10 is sectional view two of an electric toothbrush according to an embodiment of the present disclosure.
Figure 11:
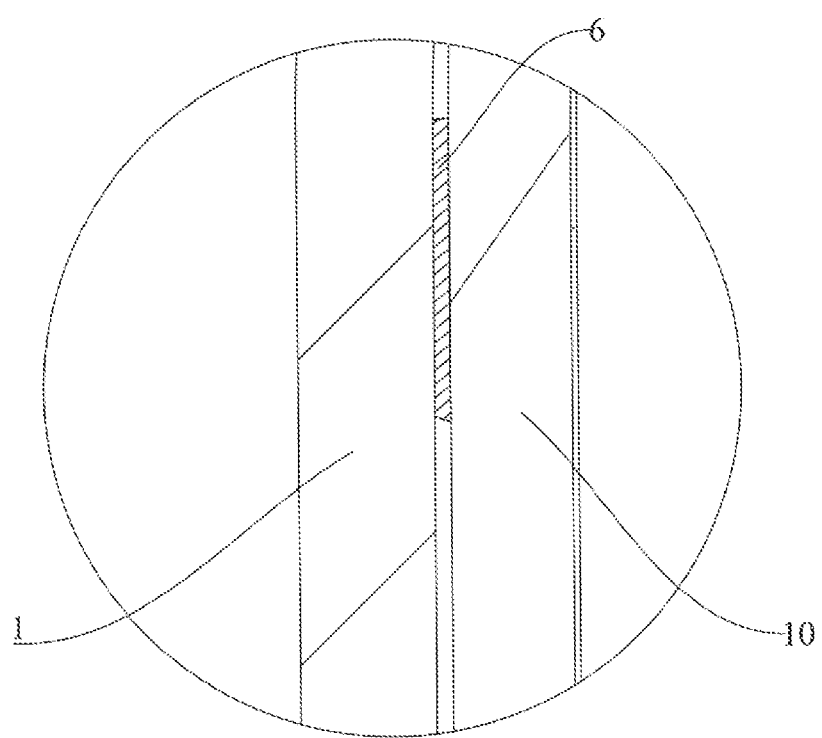
FIG. 11 is an enlarged view of a point A shown in FIG. 10 according to the present disclosure.

The sterilizing shell 1 is cylindrical in shape. Optionally, the sterilizing shell 1 is cylindrical in shape or square cylindrical in shape. In an embodiment, a shape and a size of the sterilizing shell 1 are fitted with the handle 10 of the electric toothbrush. The sterilizing shell 1 is used for being sleeved outside the electric toothbrush. In some embodiments, as shown in FIG. 1, the sterilizing shell 1 is sleeved outside part of the handle 10 and all of the brush head 20. In other embodiments, as shown in FIG. 8, the sterilizing shell 1 is sleeved outside the entire handle 10 and part of the brush head 20.

Figure 3:
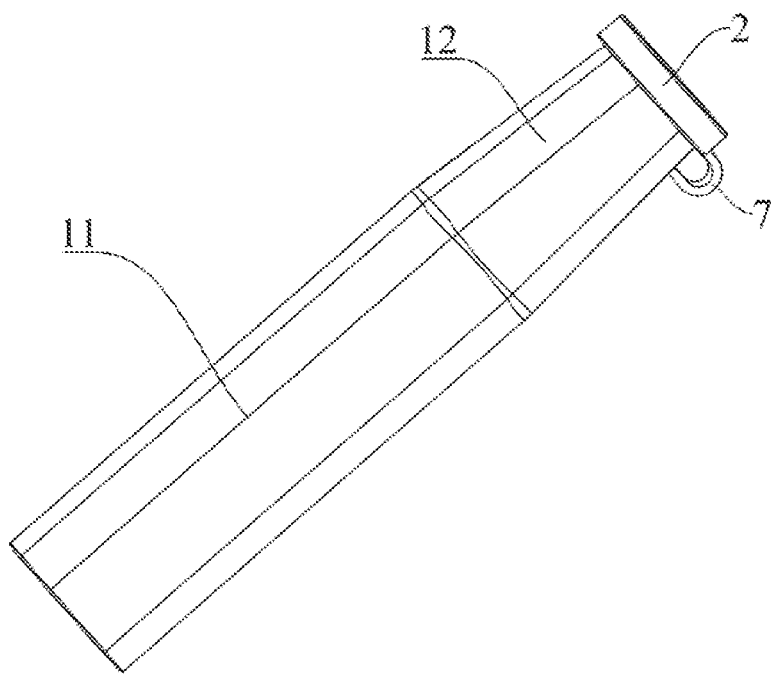
FIG. 3 is structural diagram one of a toothbrush sterilizing assembly according to an embodiment of the present disclosure.

Referring to FIG. 3, the sterilizing cover 2 is detachably connected to one end of the sterilizing shell 1, and can cover one end of the sterilizing shell 1 so as to prevent sundries such as dusts in the air from entering the sterilizing shell 1 from the one end of the sterilizing shell 1. Optionally, after the sterilizing cover 2 is connected to the sterilizing shell 1, the sterilizing cover 2 may seal one end of the sterilizing shell 1 so as to further prevent sundries such as dusts with a smaller size from entering the sterilizing shell 1 from the one end of the sterilizing shell 1.

Figure 4:
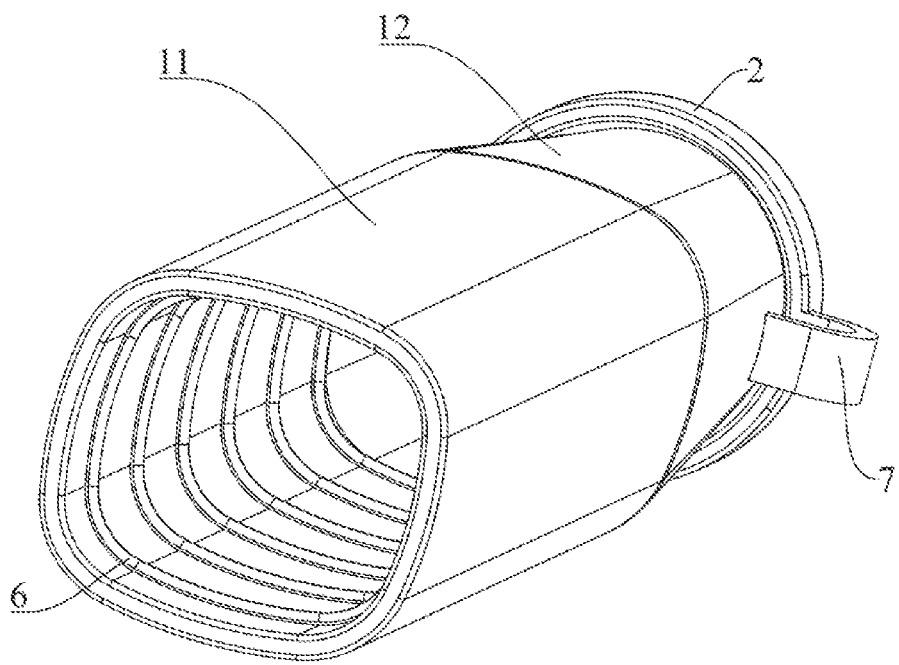
FIG. 4 is structural diagram two of a toothbrush sterilizing assembly according to an embodiment of the present disclosure.
Figure 5:
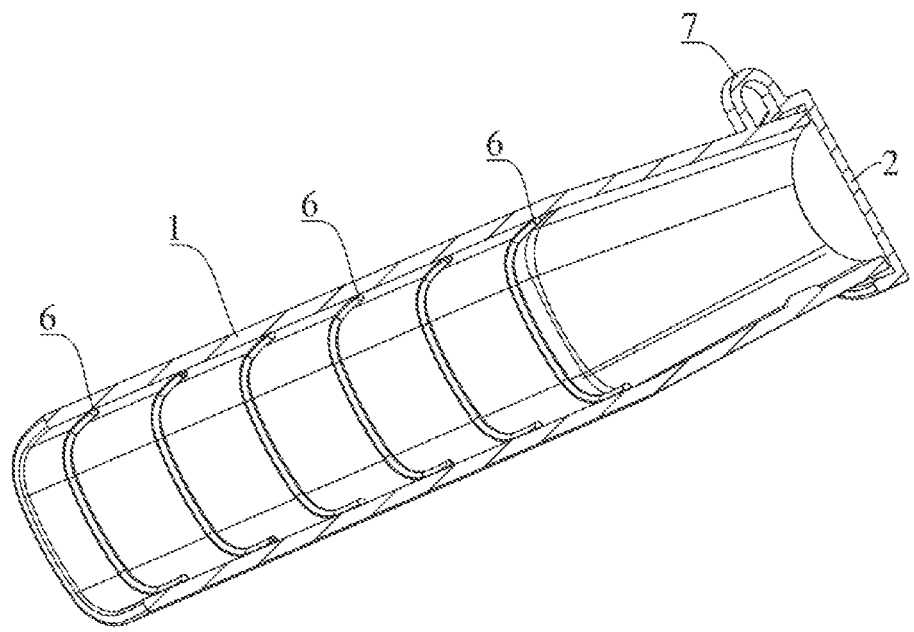
FIG. 5 is a sectional view of a toothbrush sterilizing assembly according to an embodiment of the present disclosure.

In this embodiment, the sterilizing cover 2 and the sterilizing shell 1 can be detachably connected in various ways. In some embodiments, as shown in FIGS. 4 and 5, the sterilizing cover 2 is buckled at the one end of the sterilizing shell 1, that is, one side of the sterilization cover 2 is provided with a groove. A cross-sectional area of the groove is greater than a cross-sectional area of the one end of the sterilizing shell 1, so that the one end of the sterilizing shell 1 can be clamped into the groove to realize the connection between the sterilizing cover 2 and the sterilizing shell 1. Optionally, an outer wall of the one end of the sterilizing shell 1 may have elastic protrusions for sealing a gap between a side wall of the groove and the outer wall of the sterilizing shell 1, thereby preventing sundries such as the dust, the bacteria or the like from entering the sterilizing shell 1. Further, in order to prevent the sterilizing cover 2 from being lost, as shown in FIG. 3, the toothbrush sterilizing assembly further includes a connecting part 7, one end of the connecting part 7 is connected to the outer wall of the sterilizing shell 1, and the other end of the connecting part 7 is connected to the sterilizing cover 2. The connecting part 7 is made of a soft material so as to prevent the connecting part 7 from being broken. In this embodiment, the connecting part 7 has a long strip structure. In other embodiments, the sterilizing shell 1 is connected to the sterilizing cover 2 through a screw thread. Optionally, the connecting part 7, the sterilizing shell 1 and the sterilizing cover 2 are integrally formed.

Figure 6:
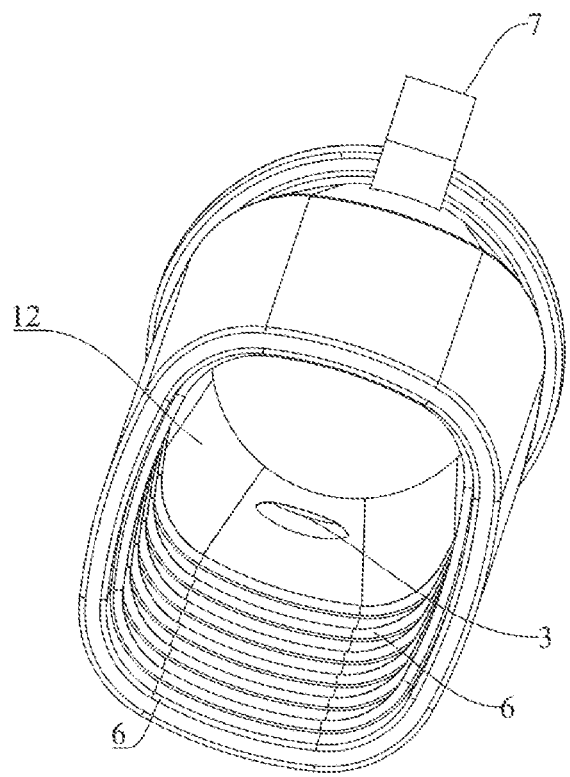
FIG. 6 is structural diagram three of a toothbrush sterilizing assembly according to an embodiment of the present disclosure.

As shown in FIGS. 2 and 6, the sterilizing element 3 is disposed on an inner wall of one end of the sterilizing shell 1 for sterilizing the brush head 20 of the electric toothbrush. The control module 4 is connected to the sterilizing element 3 and controls the sterilizing element 3 to start to sterilize a brush head 20 of the electric toothbrush. Optionally, in order to avoid energy waste, the control module 4 is used for controlling the sterilizing element 3 to start when the control module 4 determines that the brush head 20 is located within one end of the sterilizing shell 1 and the sterilizing cover 2 is connected to the one end of the sterilizing shell 1 so as to sterilize the brush head 20 and further prevent bacteria from breeding on the brush head 20. Optionally, the sterilizing element 3 is an ultraviolet electronic element. The ultraviolet electronic element can emit ultraviolet rays to the outside after being charged, and the ultraviolet rays irradiate the brush head so as to sterilize the brush head 20. In some embodiments, one sterilizing element 3 is provided. In other embodiments, multiple sterilizing elements 3 are provided, and the multiple sterilizing elements 3 are arranged in at least one of a circumferential direction and an axial direction of the sterilizing shell 1 so that sterilizing light emitted by the sterilizing elements 3 can wrap bristles of the whole brush head 20 to perform a comprehensive sterilization work.

Optionally, referring to FIG. 2, the power module 5 is electrically connected to the control module 4 and supplies electrical energy to the sterilizing element 3 through the control module 4. It can be understood that the power module 5 is also used for supplying the electrical energy to the control module 4. In some embodiments, the power module 5 may be a power source of the toothbrush sterilizing assembly itself. In this case, the toothbrush sterilizing assembly may also include a charging interface disposed on the sterilizing shell 1 for charging the power module 5. In other embodiments, the power module 5 is a power supply located within the handle 10. That is, the toothbrush sterilizing assembly shares a power source with the brush head 20. In this case, the toothbrush sterilizing assembly may also include a wireless receiving coil. The power module 5 has a wireless transmitting coil, and the power module 5 supplies the electric energy to the control module 4 and the sterilizing element 3 through the wireless transmitting coil and the wireless receiving coil. Reference can be made to the existing art for the specific connection modes and the charging principles, which is not limited in this application.

In the toothbrush sterilizing assembly provided by this embodiment, the sterilizing cover 2 is capable of being connected to the sterilizing shell 1 to form a relatively sealed space at one end of the sterilizing shell 1, and the sterilizing element 3 is also arranged within the relatively sealed space. The control module 4 can control the sterilizing element 3 to sterilize the brush head 20 located within the sealed space. The existence of the sterilizing cover 2 can prevent sundries such as the dusts from falling on the brush head. Moreover, the arrangement of the sterilizing element 3 prevents the bacteria from breeding on the brush head 20 and ensures the oral health of users.

Optionally, referring to FIG. 3, the sterilizing shell 1 includes a cylindrical body 11 and a conical body 12 which are integrally formed. The cylindrical body 11 is sleeved outside the handle 10 of the electric toothbrush and be connected to the handle 10 by a friction between the cylindrical body and the electric toothbrush. The brush head 20 is capable of being located in the conical body 12. The sterilizing cover 2 is connected to one end of the conical body 12. The sterilizing element 3 is disposed on an inner wall of the conical body 12. The conical body 12 is arranged so that the sterilizing element 3 can face the bristles of the brush head 20, facilitating performing the sterilization to the bristles.

In this embodiment, as shown in FIGS. 4 to 6, the toothbrush sterilizing assembly further includes multiple raised ribs 6, and the multiple raised ribs 6 are disposed at intervals on an inner wall of the sterilizing shell 1. The raised ribs 6 are used for increasing the friction between the sterilizing shell 1 and the handle 10 to prevent the handle 10 from being separated from the sterilizing shell 1. In addition, the raised ribs 6 can also improve the comfort degree when the user grasps the sterilizing shell 1. Optionally, the raised ribs 6 may be disposed on the inner wall of the cylindrical body 11.

Further, the raised ribs 6 are made of a soft material. When the user holds the sterilizing shell 1 for washing, according to the mechanical principle that the sterilizing shell 1 is deformed inward under force, the user's holding is not stiff, thereby ensuring flexible and firm grasping, and bringing comfortable use experience to the user. In addition, the raised ribs 6 are made of a soft material, so that the elastic deformation occurs when the raised ribs 6 are in contact with the handle 10, so that a more sealed space can be formed in the conical body 12, thereby further improving the sterilization and disinfection effect on the brush head and preventing the sterilization and disinfection failure caused by the sealing failure between the cylindrical body 11 and the handle 10. Exemplarily, the raised ribs 6 may be rubber strips, silicone strips or plastics having a hardness less than a preset hardness, that is, the raised ribs 6 are made of a rubber, silica gel, or a plastic having a hardness less than the preset hardness, which is not limited in this embodiment.

Optionally, as shown in FIG. 4, each of the raised ribs 6 extends in the circumferential direction of the sterilizing shell 1 so as to have a larger contact area with the handle 10. Further, the raised rib 6 has an annular shape.

Figure 7:
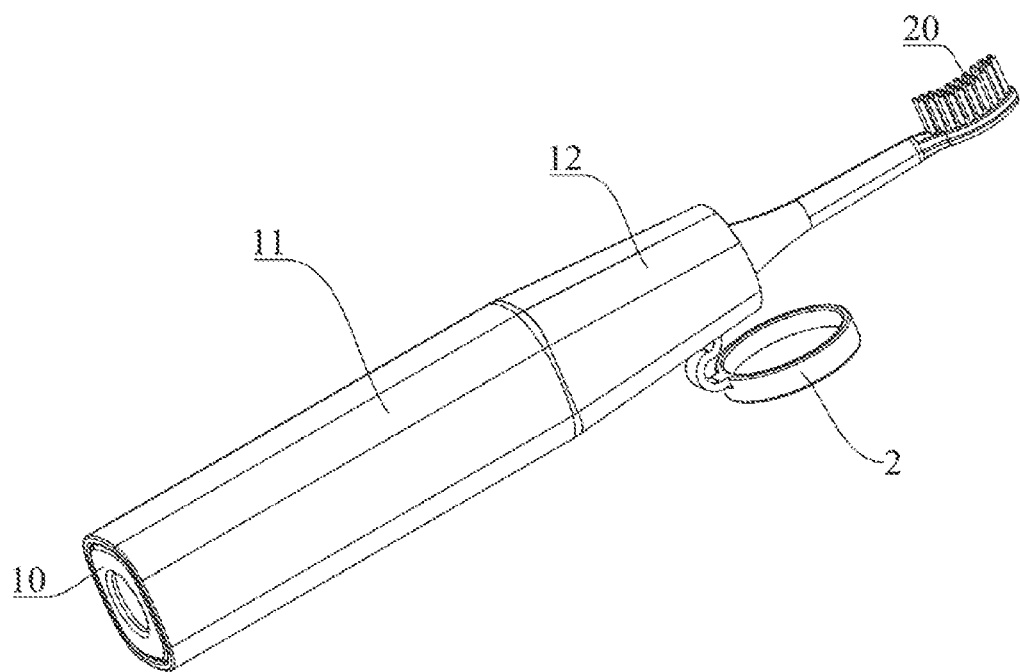
FIG. 7 is a schematic diagram of an electric toothbrush in a washing mode according to an embodiment of the present disclosure.

This embodiment also provides an electric toothbrush. As shown in FIG. 7, the electric toothbrush includes a handle 10, a brush head 20 and the above toothbrush sterilizing assembly. The sterilizing shell 1 of the toothbrush sterilizing assembly is sleeved outside the brush head 20, and the sterilizing element 3 is configured to sterilize the brush head 20.

Optionally, as shown in FIG. 8, the electric toothbrush further includes a photosensitive element 30. The photosensitive element 30 is disposed on the handle 10 or the brush head 20, and the photosensitive element 30 is communicatively connected to the control module 4 of the toothbrush sterilizing assembly. The photosensitive element 30 is used for sensing light outside the handle 10 or the brush head 20. In a case where the photosensitive element 30 senses the light outside the handle 10 or the brush head 20, the photosensitive element 30 sends a light signal to the control module 4. In this case, the control module 4 controls the sterilizing element 3 not to work. In a case where the photosensitive element 30 does not sense any light outside the handle 10 or the brush head 20, the photosensitive element 30 cannot receive a light signal. In this case, the control module 4 controls the sterilizing element 3 to work. In an embodiment, the control module 4 controls the power supply module 5 to supply electric energy to the sterilizing element 3 so that the sterilizing element 3 emits the ultraviolet rays to sterilize the brush head 20. Reference can be made to the existing art for the specific structure and work principle of the photosensitive element 30 in this embodiment, which will not be repeated in this embodiment.

In this embodiment, the handle 10 is slidably connected to the sterilizing shell 1, the electric toothbrush has a sterilizing mode and a washing mode, the sterilizing mode is shown in FIG. 1 and the washing mode is shown in FIG. 7. The control handle 10 slides relative to the sterilizing shell 1, so that the electric toothbrush switches between the sterilizing mode and the washing mode. When the electric toothbrush is in the sterilizing mode, the brush head 20 is located in the conical body 12, and the sterilizing cover 2 is connected to the sterilizing shell 1. In a case where the electric toothbrush is in the washing mode, the sterilizing cover 2 is separated from the sterilizing shell 1, and the brush head 20 extends out of the sterilizing shell 1 from one end of the sterilizing shell 1, facilitating use for the users.

The above embodiments describe only the basic principles and characteristics of the present disclosure and the present disclosure is not limited to the above embodiments. Various modifications and changes may be made in the present disclosure without departing from the spirit and scope of the present disclosure. These modifications and changes fall within the scope of the present disclosure. The scope of the present disclosure is defined by the appended claims and equivalents thereof.

What is claimed is:

1. A toothbrush sterilizing assembly, comprising:
    a sterilizing shell, which has opposite open first and second ends and is sleeved outside an electric toothbrush;
    a sterilizing cover, which is detachably connected to one end of the sterilizing shell and is capable of covering the one end of the sterilizing shell;
    a sterilizing element, which is disposed on an inner wall of the one end of the sterilizing shell;
    a control module, which is connected to the sterilizing element and configured to control the sterilizing element to start to sterilize a brush head of the electric toothbrush; and
    a power supply module, which is electrically connected to the control module; and
    wherein the sterilizing cover is buckled at the one end of the sterilizing shell and the toothbrush sterilizing assembly further comprises a connecting part, wherein the connecting part is an elastic elongated strip structure, and one end of the connecting part is connected to an outer wall of the sterilizing shell and other end of the connecting part is connected to the sterilizing cover, and
    wherein the sterilizing shell comprises a cylindrical body and a conical body which are integrally formed, the sterilizing cover is connected to one end of the conical body, and the sterilizing element is disposed on an inner wall of the conical body.

2. The toothbrush sterilizing assembly of claim 1, further comprising a plurality of raised ribs, wherein the plurality of raised ribs are disposed at intervals on the inner wall of the sterilizing shell.

3. The toothbrush sterilizing assembly of claim 2, wherein the plurality of raised ribs are rubber strips, silicone strips or plastics having a hardness less than a preset hardness.

4. The toothbrush sterilizing assembly of claim 2, wherein each of the plurality of raised ribs extends in a circumferential direction of the sterilizing shell.

5. The toothbrush sterilizing assembly of claim 1, wherein the sterilizing element is an ultraviolet electronic element and a plurality of sterilizing elements are provided.

6. An electric toothbrush, comprising a handle, a brush head and a toothbrush sterilizing assembly, wherein the toothbrush sterilizing assembly comprises:
- a sterilizing shell, which has opposite open first and second ends and is sleeved outside the electric toothbrush;
- a sterilizing cover, which is detachably connected to one end of the sterilizing shell and is capable of covering the one end of the sterilizing shell;
- a sterilizing element, which is disposed on an inner wall of the one end of the sterilizing shell;
- a control module, which is connected to the sterilizing element and configured to control the sterilizing element to start to sterilize a brush head of the electric toothbrush; and
- a power supply module, which is electrically connected to the control module,
- wherein the sterilizing shell of the toothbrush sterilizing assembly is sleeved outside the brush head, and the sterilizing element is configured to sterilize the brush head,
- wherein the sterilizing cover is buckled at the one end of the sterilizing shell and the toothbrush sterilizing assembly further comprises a connecting part, wherein the connecting part is an elastic elongated strip structure, and one end of the connecting part is connected to an outer wall of the sterilizing shell and other end of the connecting part is connected to the sterilizing cover, and
- wherein the sterilizing shell comprises a cylindrical body and a conical body which are integrally formed, the sterilizing cover is connected to one end of the conical body, and the sterilizing element is disposed on an inner wall of the conical body.

7. The electric toothbrush of claim 6, further comprising a photosensitive element, wherein the photosensitive element is disposed on the handle or the brush head and the photosensitive element is communicatively connected to the control module of the toothbrush sterilizing assembly.

8. The electric toothbrush of claim 6, wherein the handle is slidably connected to the sterilizing shell.

9. The electric toothbrush of claim 6, wherein the toothbrush sterilizing assembly further comprises a plurality of raised ribs, wherein the plurality of raised ribs are disposed at intervals on the inner wall of the sterilizing shell.

10. The electric toothbrush of claim 9, wherein the plurality of raised ribs are rubber strips, silicone strips or plastics having a hardness less than a preset hardness.

11. The electric toothbrush of claim 9, wherein each of the plurality of raised ribs extends in a circumferential direction of the sterilizing shell.

12. The electric toothbrush of claim 6, wherein the sterilizing element is an ultraviolet electronic element and a plurality of sterilizing elements are provided.

\* \* \* \* \*